United States Patent
Berton et al.

(10) Patent No.: US 9,976,927 B2
(45) Date of Patent: May 22, 2018

(54) METHOD FOR INSPECTING A CONNECTION SEAL BETWEEN TWO PARTS

(71) Applicant: SAFRAN AIRCRAFT ENGINES, Paris (FR)

(72) Inventors: Joël Yvan Marcel Robert Berton, Hericy (FR); Pascal Cendrier, Boussy Saint Antoine (FR)

(73) Assignee: SAFRAN AIRCRAFT ENGINES, Paris (FR)

( * ) Notice: Subject to any disclaimer, the term of this patent is extended or adjusted under 35 U.S.C. 154(b) by 0 days. days.

(21) Appl. No.: 15/508,723

(22) PCT Filed: Sep. 1, 2015

(86) PCT No.: PCT/FR2015/052311
§ 371 (c)(1),
(2) Date: Mar. 3, 2017

(87) PCT Pub. No.: WO2016/034808
PCT Pub. Date: Mar. 10, 2016

(65) Prior Publication Data
US 2017/0284889 A1    Oct. 5, 2017

(30) Foreign Application Priority Data
Sep. 4, 2014 (FR) ..................... 14 58261

(51) Int. Cl.
*G01M 3/22* (2006.01)
*G01M 3/14* (2006.01)
(Continued)

(52) U.S. Cl.
CPC ............ *G01M 3/221* (2013.01); *G01M 3/141* (2013.01); *G01N 21/91* (2013.01); *G01N 1/286* (2013.01);
(Continued)

(58) Field of Classification Search
CPC .. G01N 21/8803; G01N 21/91; G01N 21/954; G01N 1/286; G01N 2001/2873;
(Continued)

(56) References Cited

U.S. PATENT DOCUMENTS 3,652,225 A * 3/1972 Coffin, Jr. ............. G01N 21/91
148/273
3,957,538 A * 5/1976 Fairweather .......... H01M 2/065
429/171
(Continued)

OTHER PUBLICATIONS

International Search Report as issued in International Patent Application No. PCT/FR2015/052311, dated Nov. 5, 2015.
(Continued)

*Primary Examiner* — Randy Gibson
*Assistant Examiner* — Gedeon M Kidanu
(74) *Attorney, Agent, or Firm* — Pillsbury Winthrop Shaw Pittman LLP

(57) ABSTRACT

A method for checking a connection seal between two elements of a part, includes dipping the part to be checked in a penetrant having a compound suitable for reacting to light excitation; cutting the part at the connection to be checked; and checking for the presence of penetrant under a light capable of exciting the penetrant.

8 Claims, 2 Drawing Sheets

(51) Int. Cl.
  *G01N 30/00* (2006.01)
  *G01N 21/91* (2006.01)
  *G01N 1/28* (2006.01)

(52) U.S. Cl.
  CPC ..... *G01N 30/00* (2013.01); *G01N 2001/2873* (2013.01)

(58) Field of Classification Search
  CPC .......... G01N 2291/0234; G01M 3/221; G01M 3/141
  USPC .......................................................... 73/865
  See application file for complete search history.

(56) References Cited

U.S. PATENT DOCUMENTS

| | | | | |
|---|---|---|---|---|
| 4,621,193 | A * | 11/1986 | Van Hoye | B05B 11/0035 250/302 |
| 4,944,185 | A * | 7/1990 | Clark, Jr. | G01N 29/12 324/214 |
| 5,115,136 | A * | 5/1992 | Tomasch | G01N 21/8803 250/302 |
| 6,427,544 | B1 * | 8/2002 | Sanders | G01N 21/91 250/302 |
| 7,543,513 | B2 * | 6/2009 | Kobayashi | C04B 35/565 73/865.9 |
| 7,794,395 | B2 * | 9/2010 | Bonningue | G01N 21/91 250/365 |
| 2004/0168640 | A1 * | 9/2004 | Muto | C23C 4/02 118/728 |
| 2005/0063784 | A1 * | 3/2005 | Nickelson | B09B 1/00 405/129.57 |
| 2006/0186260 | A1 * | 8/2006 | Magnuson | B64F 5/60 244/1 R |
| 2006/0225508 | A1 * | 10/2006 | Sfeir | G01B 17/02 73/602 |

OTHER PUBLICATIONS

Salot, W. J., "Mystery Leaks in a 1500 PSIG Waste Heat Boiler," ip.com Journal, ip.com Inc., Sep. 2012, XP013153773, 14 pages.
Long, N., et al., "Detection of Hermetic Defects in HTS Wire," IEEE Transactions on Applied Superconductivity, vol. 15, No. 2, Jun. 2005, XP011134230, pp. 3672-3675.
International Preliminary Report on Patentability and the Written Opinion of the International Searching Authority as issued in International Patent Application No. PCT/FR2015/052311, dated Mar. 7, 2017.

* cited by examiner

METHOD FOR INSPECTING A CONNECTION SEAL BETWEEN TWO PARTS

CROSS-REFERENCE TO RELATED APPLICATIONS

This is the U.S. National Stage of PCT/FR2015/052311, filed Sep. 1, 2015, which in turn claims priority to French Patent Application No. 1458261, filed Sep. 4, 2014, the entire contents of all applications are incorporated herein by reference in their entireties.

TECHNICAL FIELD OF THE INVENTION

The field of the invention is that of the inspection of a connection seal between two parts which must be strictly hermetic.

The invention finds a particularly interesting application in the field of aeronautics and in particular enables a check to be made that the wires and sleeves of the wiring harnesses of a turbomachine are correctly bonded.

TECHNOLOGICAL BACKGROUND OF THE INVENTION

It is known to inspect the seal, or tightness, of a connection between two glued elements using a non-destructive inspection method consisting in detecting a leak of a tracer gas such as, for example, helium.

However, this inspection method requires that sophisticated and expensive devices are purchased.

GENERAL DESCRIPTION OF THE INVENTION

Against this background, the invention is intended to provide a solution to the problem mentioned above, such that inspections of the seals of a connection between two glued elements may be made simply, rapidly and economically.

To this end the invention relates to a method for inspecting the seal of a connection between two elements of a part comprising:
- a step of dipping the part to be inspected in a penetrant containing a compound of a kind which will react to light excitation;
- a step of cutting said part where the connection to be inspected is located;
- a step of checking for the presence of penetrant under a light capable of exciting said penetrant where said cut has been made.

The method according to the invention is a destructive inspection method which should be differentiated from the known non-destructive inspection methods of the state of the art. The method according to the invention thus enables the purchase of complex and costly equipment to be avoided. The method according to the invention is a simple, rapid, reliable method requiring only few resources and little equipment, which also occupy a small volume, compared with the sophisticated devices using helium.

The inspection method according to the invention may also have one or more of the characteristics below, considered individually, or in all technically possible combinations:

said method includes, prior to the step of cutting, a step of rinsing the part to be inspected;

said method includes a step of drying said part to be inspected after said step of rinsing;

said penetrant contains a compound containing fluorescein emitting a reflected fluorescent light when the penetrant is excited by ultraviolet rays;

said method is a method for inspecting the seal of a connection between two elements which have been rigidly connected to one another by glueing;

said method is a method for inspecting the seal of a connection made by glueing between an elastomer sleeve and a wire of an electric harness of a turbomachine;

said method is a method for inspecting the seal of a connection made by glueing between a fluoroelastomer sleeve and a wire of an electric harness of a turbomachine.

Another object of the invention is a method for inspecting the seal of a batch of parts including a step of taking a sample of parts from said batch, and a step of inspecting the sample taken according to the invention.

The invention will be better understood from the following description.

BRIEF DESCRIPTION OF THE FIGURES

Other characteristics and advantages of the invention will be seen clearly on reading the description below, with reference to the appended figures.

DETAILED DESCRIPTION OF IMPLEMENTATIONS OF THE INVENTION

Figure 1:
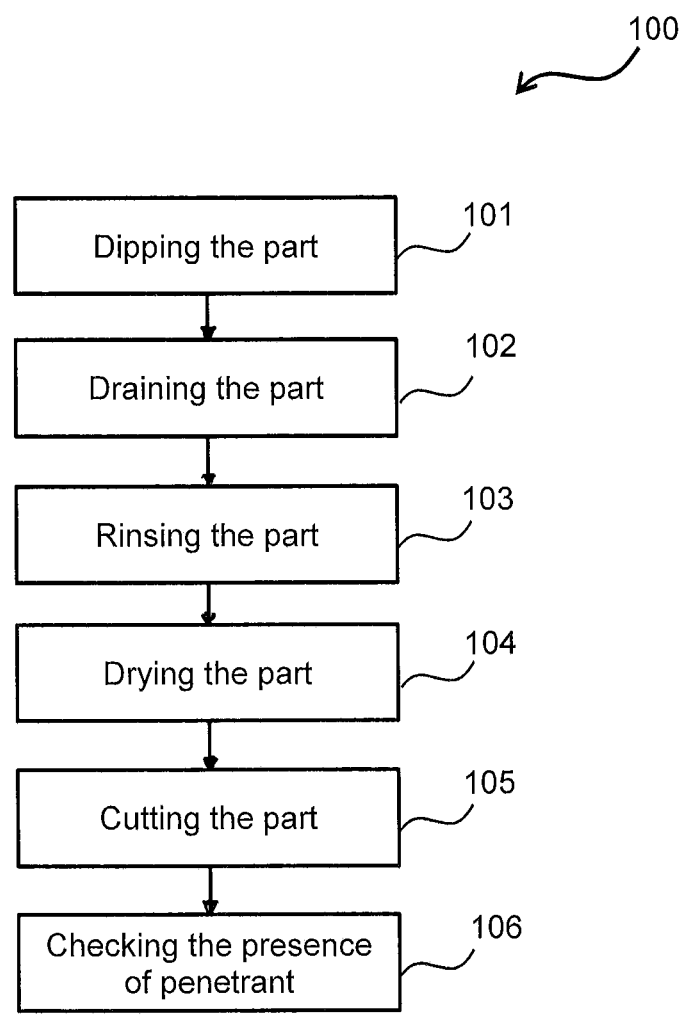
FIG. 1 is a block diagram illustrating the various steps of the method according to the invention.

With reference to FIG. 1, inspection method 100 according to the invention enables the satisfactory bonding of a connection made by glueing between two parts to be checked, by inspecting the seal or tightness of the connection.

Figure 2:
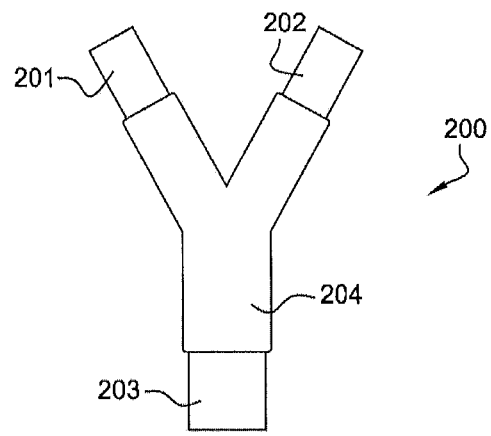
FIG. 2 represents a part to be inspected using the method according to the invention.

FIG. 2 illustrates an example of a part to be inspected using the method according to the invention. This part is a portion 200 of an electrical harness (not represented in its entirety) of a turbomachine at a Y-shaped coupling connecting three wires 201, 202 and 203 of a wiring harness. In this Y-shaped coupling a sleeve 204 made of elastomer, for example of the fluoroelastomer type, is glued in such a way that the parts of wires 201, 202 and 203 inside Y-shaped sleeve 204 are made strictly hermetic from outside.

First step 101 of inspection method 100 according to the invention consists in dipping part 200 to be inspected in a penetrant fluid bath for a predetermined period, where the dipping period is predetermined according to level of hermeticity to be inspected.

The penetrant fluid is a liquid containing, for example, a compound of a kind which will react to light excitation. For example, the compound may be a coloured compound, and ideally a fluorescent compound, which emits a reflected fluorescent light when the compound is excited by a light source.

The penetrant fluid advantageously contains fluorescein emitting a reflected fluorescent light when it is excited by an ultraviolet light source.

An aperture of several micrometers in the connection is sufficient to allow the penetrant fluid to penetrate and, under capillary action, it will penetrate to the bottom of the connection's aperture.

Second step 102 of method 100 consists in draining part 200.

Third step 103 of method 100 consists in rinsing the part, for example in water.

Fourth step 104 of the method consists in drying part 200 by appropriate means provided for this purpose.

Figure 3:
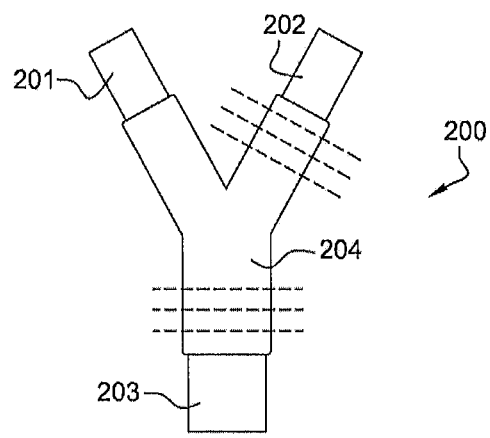
FIG. 3 illustrates the part to be inspected in the fifth step of the inspection method according to the invention.

Fifth step 105 of the method consists in making cross-sections or cuts in part 200 in the areas where sleeve 204 and wires 201, 202, 203 are glued. Advantageously, several cross-sections are made, to check whether or not the penetrant fluid is present in various locations of part 200. In this connection, FIG. 3 illustrates an example of locations of cross-sections which can be made on part 200. Inspection consists in observing after cutting whether penetrant fluid is present in the connection. If this is so it reveals that the connection is not therefore sealed.

Sixth step 106 consists in checking whether the penetrant fluid is present by means of an exciting light source in the different sections made during previous step 105. Use of a penetrant fluid containing a coloured compound, ideally a fluorescent one, thus enables it to be revealed easily whether the penetrant is present in the connection to be inspected.

Advantageously, the inspection method according to the invention enables a check to be made that a connection made by glueing between an elastomer sleeve, for example made of fluoroelastomer, and at least one wire of a wiring harness of a turbomachine, is satisfactorily hermetic.

The term "glueing" is understood to mean a bonding technique which may involve an adhesive, a cement or a sealing compound ("potting") as an intermediate product between the elements of the connection to be inspected. This intermediate bonding product is chemically compatible with the respective materials of the elements which are to be connected.

The invention has applications:
  when developing an assembly comprising a bonded connection between several elements, thereby enabling the connection's bonding parameters to be confirmed;
  during an examination, in order to ascertain the limits of an aperture for a bonded connection.

The invention is used to inspect the seals of all connections using the penetrant fluid. In particular, a probe, a unit or a sealed assembly containing a connection which is presumed to be hermetic or sealed can undergo such an inspection treatment.

The invention claimed is:

1. A method for inspecting a connection seal between two elements of a part, the method comprising:
   dipping the part to be inspected in a penetrant containing a compound that reacts to light excitation;
   cutting said part where the connection to be inspected is located;
   checking a cut section of the connection for a presence of the penetrant inside the connection under a light capable of exciting said penetrant.

2. The inspection method according to claim 1, wherein said penetrant contains a compound containing fluorescein emitting a reflected fluorescent light when the penetrant is excited by ultraviolet rays.

3. The inspection method according to claim 1, wherein said method is a method for inspecting the seal of a connection between two elements which have been rigidly connected to one another by gluing.

4. The inspection method according to claim 1, wherein said method is a method for inspecting the seal of a connection made by gluing between an elastomer sleeve and a wire of an electric harness of a turbomachine.

5. The inspection method according to claim 1, wherein said method is a method for inspecting the seal of a connection made by gluing between a fluoroelastomer sleeve and a wire of an electric harness of a turbomachine.

6. A method for inspecting a seal of a batch of parts comprises taking a sample of parts from said batch and performing the method for inspecting the sample according to claim 1.

7. The inspection method according to claim 1, further comprising, prior to the cutting, rinsing the part to be inspected.

8. The inspection method according to claim 7, further comprising drying said part to be inspected after said rinsing.

* * * * *